(12) United States Patent
Gerlach et al.

(10) Patent No.: US 6,564,646 B1
(45) Date of Patent: May 20, 2003

(54) MEASURING METHOD FOR DETERMINING THE BIAXIAL SHAPING BEHAVIOR OF METALLIC MATERIALS, MORE PARTICULARLY SHEET METAL

(75) Inventors: Jörg Gerlach, Duisburg (DE); Klaus Blümel, Dinslaken (DE)

(73) Assignee: Thyssen Stahl AG, Duisburg (DE)

( * ) Notice: Subject to any disclaimer, the term of this patent is extended or adjusted under 35 U.S.C. 154(b) by 0 days.

(21) Appl. No.: 09/194,999

(22) PCT Filed: Jun. 25, 1997

(86) PCT No.: PCT/EP97/03324

§ 371 (c)(1),
(2), (4) Date: Jan. 4, 1999

(87) PCT Pub. No.: WO98/00699

PCT Pub. Date: Jan. 8, 1998

(30) Foreign Application Priority Data

Jun. 29, 1996 (DE) .......................................... 196 26 242

(51) Int. Cl.⁷ ........................... G01D 1/16; G01N 19/08
(52) U.S. Cl. ........................................... 73/789; 73/799
(58) Field of Search ........................ 73/825, 826, 789, 73/796, 797, 804, 818, 822, 840, 763, 799, 812

(56) References Cited

U.S. PATENT DOCUMENTS

| | | | | | |
|---|---|---|---|---|---|
| 3,554,019 A | * | 1/1971 | Hove et al. | ..................... | 73/826 |
| 5,105,626 A | * | 4/1992 | Gonczy et al. | ................ | 73/826 |
| 5,905,204 A | * | 5/1999 | DeGiorgi et al. | .............. | 73/826 |

FOREIGN PATENT DOCUMENTS

| DE | 36 17 455 A1 | 11/1987 |
|---|---|---|
| DE | 39 14 966 C1 | 7/1990 |
| WO | WO 90/13804 | 11/1990 |

* cited by examiner

Primary Examiner—Max Noori
(74) Attorney, Agent, or Firm—Proskauer Rose LLP

(57) ABSTRACT

The invention relates to a method of measuring the biaxial shaping behaviour of metal materials, more particularly sheet metal. In the measuring method a flow locus curve comprehensively describing the shaping behaviour of the material is determined by determining the flow limits under tensile and compressive loading of secondary samples of a primary sample previously subjected to at least tensile, but preferably also to compressive loading. Preferably a number of flow locus curves of different preliminary loading of the primary sample are determined for each material. These flow locus curves, completely ascertained by tests, provide the further processor with a reliable ancillary means of selecting a material required for the particular shaping operation.

7 Claims, 5 Drawing Sheets

AF0: INITIAL FLOW LOCUS CURVE
FF01: SECONDARY FLOW LOCUS CURVE
FF02:

a, b: SEMIAXIS OF THE ELLIPSE
α: ANGLE OF INCLINATION
u, v: AXIS DISPLACEMENTS OF THE CENTER OF THE ELLIPSE $\varepsilon_{V1} < \varepsilon_{V2} < \varepsilon_{V3} < \varepsilon_{V4}$ $\varepsilon_{V1} < \varepsilon_{V2} < \varepsilon_{V3} < \varepsilon_{V4}$

MEASURING METHOD FOR DETERMINING THE BIAXIAL SHAPING BEHAVIOR OF METALLIC MATERIALS, MORE PARTICULARLY SHEET METAL

BACKGROUND OF THE INVENTION

For many years a need has existed to describe comprehensively the shaping behavior of metallic materials, more particularly sheet metal, for different kinds and degrees of shaping. If the producer of materials could himself successfully provide such a comprehensive description, further processors would have a simple basis on which to discover the material best suitable for a particular shaping operation. A comprehensive description of the shaping behavior of a material is also a precondition for the use of numerical methods in shaping technology for investigations of manufacturability and for the simulation of the shaping process. To ensure that suitable materials are chosen and also that such numerical methods and simulations lead to reliable results, the shaping behavior must be completely ascertained by tests, nor must it be partially based on hypotheses.

It is particularly difficult to predict the behavior of a material during the shaping of metal sheets in shaping tools, since stress conditions are set up in the deformation zones which are the result of different overlayered loadings, such as tensile, compressive and bending stresses. In idealised pure deep-drawing the material is only allowed to flow from the edge of a disc-shaped workpiece (circular blank in the art), without the center itself being shaped. In ideal stretch forming no flow of material from the edge of the circular blank is allowed, so that all the deformation takes place exclusively in the central zone. In practice there is no idealized deep-drawing or stretch forming, but deep-drawing and stretch forming overlayer one another. Workpieces mainly produced by deep-drawing are called deep-drawn parts, while workpieces mainly produced by stretch drawing are called stretch-drawn parts. In vehicle building deep-drawn parts are, for example, half-shells for oil sumps and fuel tanks, the inner parts of doors and wheel casings, while stretch-drawn parts include engine cowlings, doors, roofs, flaps and covers.

Failure has marked all the previously known methods of predicting the behavior of material with different degrees of deformation and a combination of different loadings such as occur in actual stretch-drawn or deep-drawn parts.

The experimental determination of the biaxial behavior of sheet metals under varying tensile stresses is known (DE 39 14 966 C1; WO 90/13804). In this prior art measuring method overlength, longitudinally slotted sample arms connected crosswise to flat samples are used to introduce thereinto for testing purposes the tensile forces which lead to a homogeneous plastic deformation of the sample central area, forming the actual measuring zone. However, the achievement of a homogeneous distribution of stresses in the measuring zone, which is a precondition for clear measuring results, can be obtained on such a sample only by taking very expensive constructional steps concerning the connected sample arms. There is in addition the disadvantage that with this measuring method a result is obtained only concerning flow behavior in two axial directions under tensile stress. No indication of flow behavior under compression can be obtained, since the application of compressive stressing would bend apart the overlength, longitudinally slotted sample arms.

Furthermore, it is known to determine the biaxial shaping behavior of metal sheets experimentally (J. V. Laukonis, Metallurgical Trans. A, Vol. 12A (March 1981), pp 467–472), wherein first of all a zone of substantially homogeneous deformation is produced by tensile stressing in a primary sample. A number of secondary samples with different orientation to the axis of the tensile stressing are taken from this zone of substantially homogeneous deformation of the primary sample. The tensile flow limit is determined in the secondary samples under uniaxial tensile stressing. As in the case of the previous method, this method also provides only an indication concerning flow behavior in two axial directions under tensile stress.

Compressive loading can also be applied using another prior art measuring apparatus for the biaxial static and/or dynamic tensile loading of laminar square metal samples (DE 36 17 455 A1). For this purpose force-introducing elements are directly connected to the four sides of the metal sample. It is questionable whether tensile loading initiated thereby leads to homogeneous plastic deformation in the sample central area forming the actual measuring zone. Any investigation of the shaping behavior of thin sheet materials with a combination of tensile and compressive stresses seems impossible, since the laminar samples of material are unstable and bend apart even under low compressive forces.

SUMMARY OF THE INVENTION

It is an object of the invention to develop a simply performable measuring method for determining the biaxial shaping behavior of metal materials, more particularly with a combination of tensilen and compressive stressings. More especially, the shaping behavior determined gives the user of available materials a new possibility of describing typical kinds of stressing, such as deep drawability or stretch drawability.

This problem is solved according to the invention by the following method steps:

a) An area of practically homogeneous deformation is produced in a primary sample at least by uniaxial tensile stressing.

b) A number of secondary samples with different orientation to the axis of tensile stressing are taken from the area of practically homogeneous deformation of the primary sample.

c) The tensile and compressive flow limits are determined in the secondary samples under uniaxial tensile and compressive loading.

d) The relationship of plastic longitudinal and transverse expansion is determined at the tensile and/or compressive flow limit in at least one secondary sample.

e) The parameters of an at least approximately elliptical flow locus curve describing the shaping behavior of the material are determined using the flow limits determined and the relationship determined at the tensile and/or compressive flow limit.

In comparison with other methods, the expense of the measuring method according to the invention is considerably reduced by the fact that a start is made from an only approximately homogeneous area of deformation, from which the secondary samples are removed for determining the parameters of the elliptical flow locus curve. Of course, it is enough to determine five parameters to define an ellipse locus of the flow limit in all four quadrants of the tensile/compressive area. This flow locus curve provides the further processor with the working means which he needs for the selection of the suitable material for the particular shaping operation, and also for computerised investigations of manufacturability and simulations of shaping behavior.

Preferably during tensile loading the primary sample is simultaneously subjected to compressive stressings, more particularly by upsetting, transversely of the tensile loading. The degree of compressive stressing (upsetting) is maintained constant in the zone of substantially homogeneous deformation. The tensile loading and simultaneous upsetting can be performed in a known and established manner in a wedge-draw test. Preferably as a variant of the known wedge-draw test, not rigid lateral cheeks are used (DE-PS 527 122), but large-size rollers, with which there is practically no edge friction of the primary sample disadvantageous to homogeneous deformation. With the apparatus for the wedge-draw test, the constant degree of upsetting can readily be put into effect by the material having a constant original width in the zone of the subsequent homogeneous deformation.

According to the invention the interest of the further processor of the material in its behavior with different degrees of deformation can be satisfied by subjecting a number of primary samples of material to variously heavy preliminary deformations (degrees of upsetting). The various elliptical flow locus curves thus obtained then give an engineer in the art an indication of how the material behaves with different degrees of deformation.

For the most precise determination possible of the flow locus curves it has become the established practice to use not the usual flow limit, which is 0.2% plastic elongation (0.2% proof stress), but to use a flow limit of 0.02%, which is close to the technical proof stress (0.01%). This substantially lower proof stress also permits the use of relatively thin sheets, thus reducing the risk of their easily bending apart when the compressive flow limit is determined.

BRIEF DESCRIPTION OF THE DRAWINGS

The invention will now be explained in greater detail with reference to the embodiment thereof illustrated in the drawings, which show.

DETAILED DESCRIPTION OF THE INVENTION

A metal sheet prepared as a primary sample for a wedge-draw test and having a thickness of 0.7 to 3.5 mm consisted of a slim wedge portion 1 having a $\alpha_k=2°$ and a portion 2 of constant width. Following the wedge-draw test, the portion 2 of constant width comprised the area of substantially homogeneous deformation.

Figure 2:
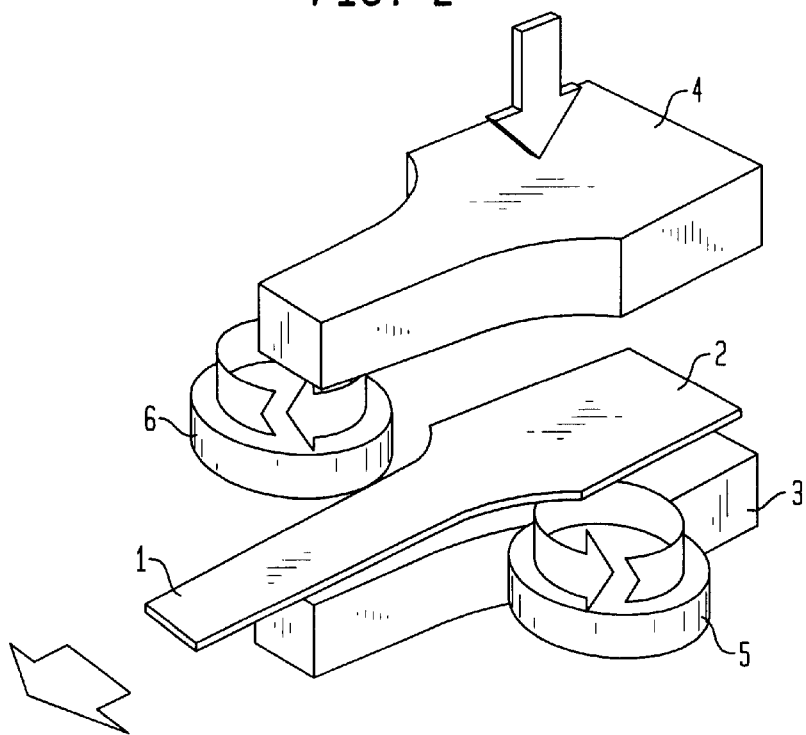

In the wedge-draw test (FIG. 2) the primary sample was supported at its wide sides by guide plates 3, 4. The narrow sides of the primary sample were acted upon by large-size rollers 5, 6, which for different wedge-draw tests were either adjustable to a different spacing in the case of primary samples of identical dimensions, or adjusted to a constant roller spacing in the case of primary samples having portions 2 of different widths, so as to obtain in any case different degrees of upsetting in the portion 2 of constant width as the primary sample was drawn through.

Figure 1:
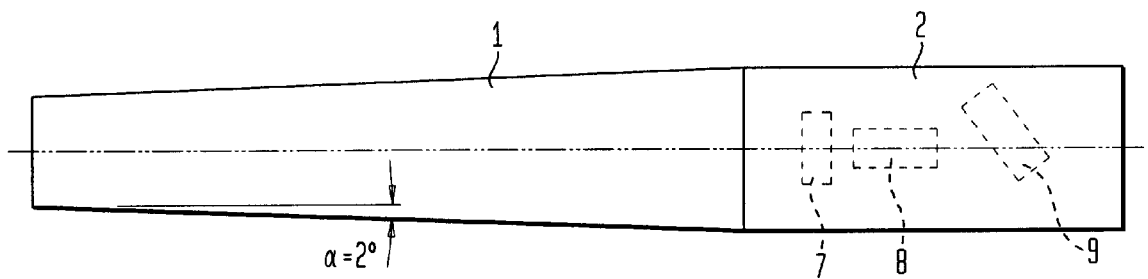
FIG. 1 a primary sample in the form of a sheet metal strip having a wedge angle $\alpha_k=2°$ and a portion of constant width, FIG. 2 a diagrammatic presentation of a wedge-draw test with a primary sample, FIG. 3 a plan view of a secondary sample, FIG. 4 elliptical locus curves of material whose primary samples were upset in the wedge-draw test with different degrees of upsetting, FIG. 5 a characteristic elliptical flow locus curve with elements determining the matter, FIG. 6 characteristic flow locus curves of three different materials whose primary samples were predeformed with two different degrees of upsetting, FIG. 7 different flow locus curves with a semiaxis relation a/b<1.8 of a stretch-drawn steel, whose primary samples were upset in the wedge-draw test with different degrees of upsetting, and FIG. 8 different flow locus curves with a semiaxis relation a/b>2 of a soft deep-drawn steel, whose primary samples were upset in the wedge-draw test with different degrees of upsetting.
Figure 3:
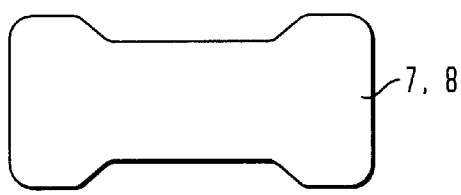
Figure 4:
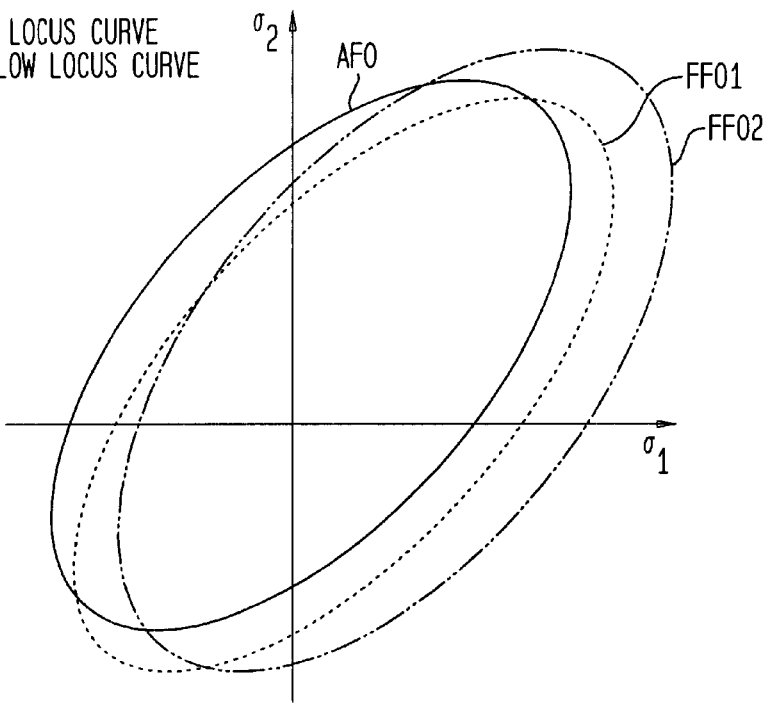

Following the wedge-draw test, secondary samples 7, 8 of identical size but different orientation were taken from the primary sample, as indicated in FIG. 1. Secondary sample 7 lay with its axis transversely of the axis of the primary sample 1, while secondary sample 8 lay with its axis parallel with the axis of the primary sample 1. The special shape of the individual secondary samples 7,8 can be gathered from FIG. 3. In total the two secondary samples were taken, namely a sample 7 and a sample 8. The samples 7 and 8 were each subjected to a uniaxial tensile loading and a uniaxial compressive loading. The flow limits of $\sigma_1$, $-\sigma_1$, $\sigma_2$ and $-\sigma_2$ determined with a plastic elongation of 0.02% are the geometrical loci of the elliptical flow locus curve on the axes of the stress area (main plane of stress). FIG. 4 shows the points of a drawn-out flow locus curve of a material. On their own the points $\sigma_1$, $-\sigma_1$, $\sigma_2$ and $-\sigma_2$ are not enough to determine the elliptical flow locus curve. For the complete determination of the elliptical flow locus curve, therefore, a further measured value is required, for example, the pitch of the tangent to the elliptical flow locus curve at the point of intersection with one of the axes $\sigma_1$, $\sigma_2$. The pitch is determined by determining in at least one secondary sample the relation of plastic longitudinal and transverse elongation at the tensile and/or compressive flow limit.

Figure 5:
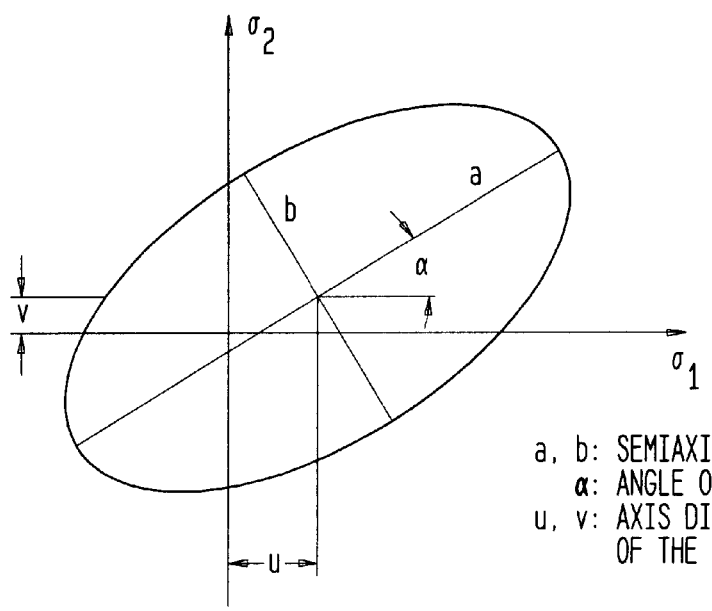

As a result, the elliptical flow locus curve, with its axes a, b, its displacement of center u, v and its angle of inclination α are then clearly circumscribed, as shown in FIG. 5.

Figure 6:
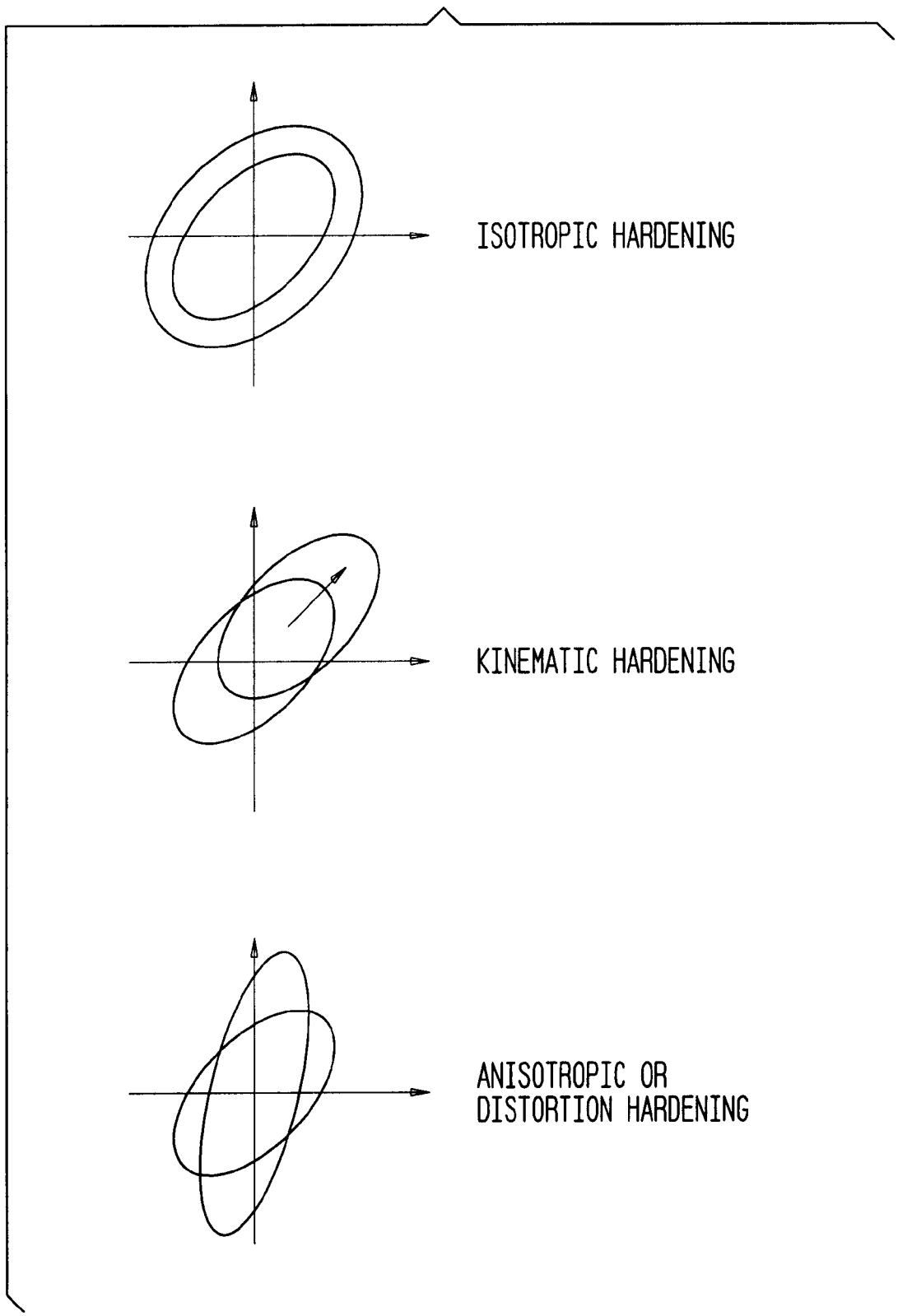

FIG. 4 shows, as well as the drawn-out elliptical flow locus curve, other flow locus curves FF01, FF02. The flow locus curves FF01 and FF02 are associated with different primary samples of the same material which, however, were subjected to different degrees of deformation (degrees of upsetting). A comparison between these flow locus curves enables statements to be made confirming the deformation behavior of the material:

Thus FIG. 6, corresponding to FIG. 4, shows elliptical flow locus curves with different degrees of deformation for different materials. A distinction is drawn between isotropic hardening (widening of the flow surface on all sides), kinematic hardening (rigid body movement of the flow surface) and distortion hardening (change of inclination and/or change of semiaxis relation).

It was found that for stretch drawing materials were best suited with only very small displacements of center in the positive or negative direction in the state as delivered $$\frac{u}{R_{p\,0.02}}, \frac{v}{R_{p\,0.02}} < 20\%$$

with a semiaxis relation a/b<1.85.

Figure 7:
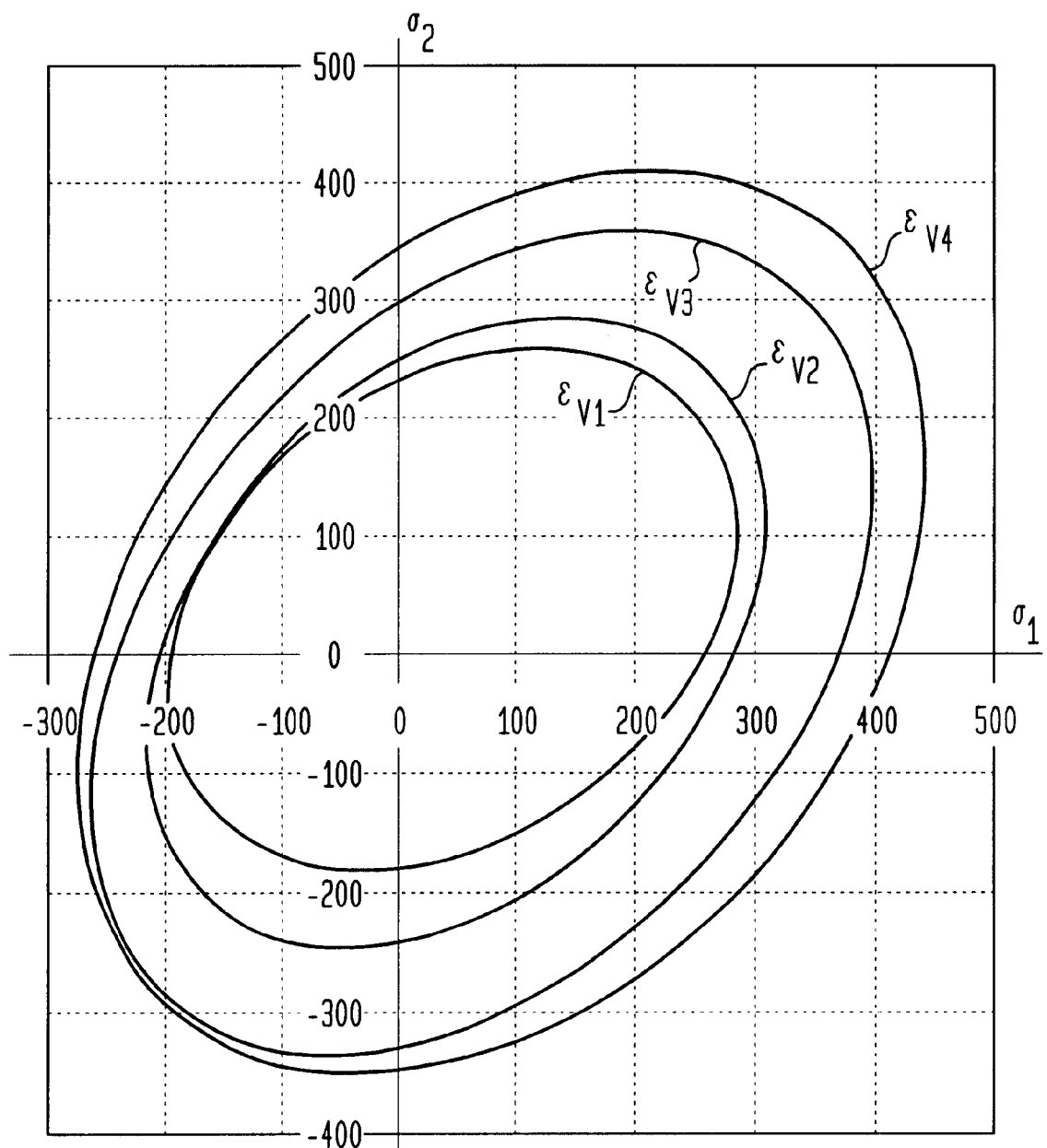

FIG. 7 shows elliptical flow locus curves of a material for stretch-drawn parts—i.e., parts which during deformation were mainly subjected to stretch-drawing stressing. The parameters $\epsilon_{V1}$, $\epsilon_{V2}$, $\epsilon_{V3}$, $\epsilon_{V4}$ for the various flow location curves represent the comparative plastic elongation with different states of deformation (degrees of upsetting) of the primary samples 1–4. Allowing for the volumetric constant in plastic shaping, the comparative elongation is defined as follows:

$$\varepsilon_v = \sqrt{\frac{4}{3}(\varepsilon_{1plast}^2 + \varepsilon_{1plast}\varepsilon_{2plast} + \varepsilon_{2plast}^2)}$$

where $\epsilon_{1plast}$ is the true plastic elongation, determined from the elongation of the homogeneous zone of the primary sample, and $\epsilon_{2plast}$ is the true plastic elongation, determined from the upsetting of the homogeneous zone of the primary sample.

It was also discovered that materials having a semiaxis ratio a/b>2 are particularly well suited to deep drawing processes. This positive suitability is further increased if the aforementioned displacement of center >20%.

Figure 8:
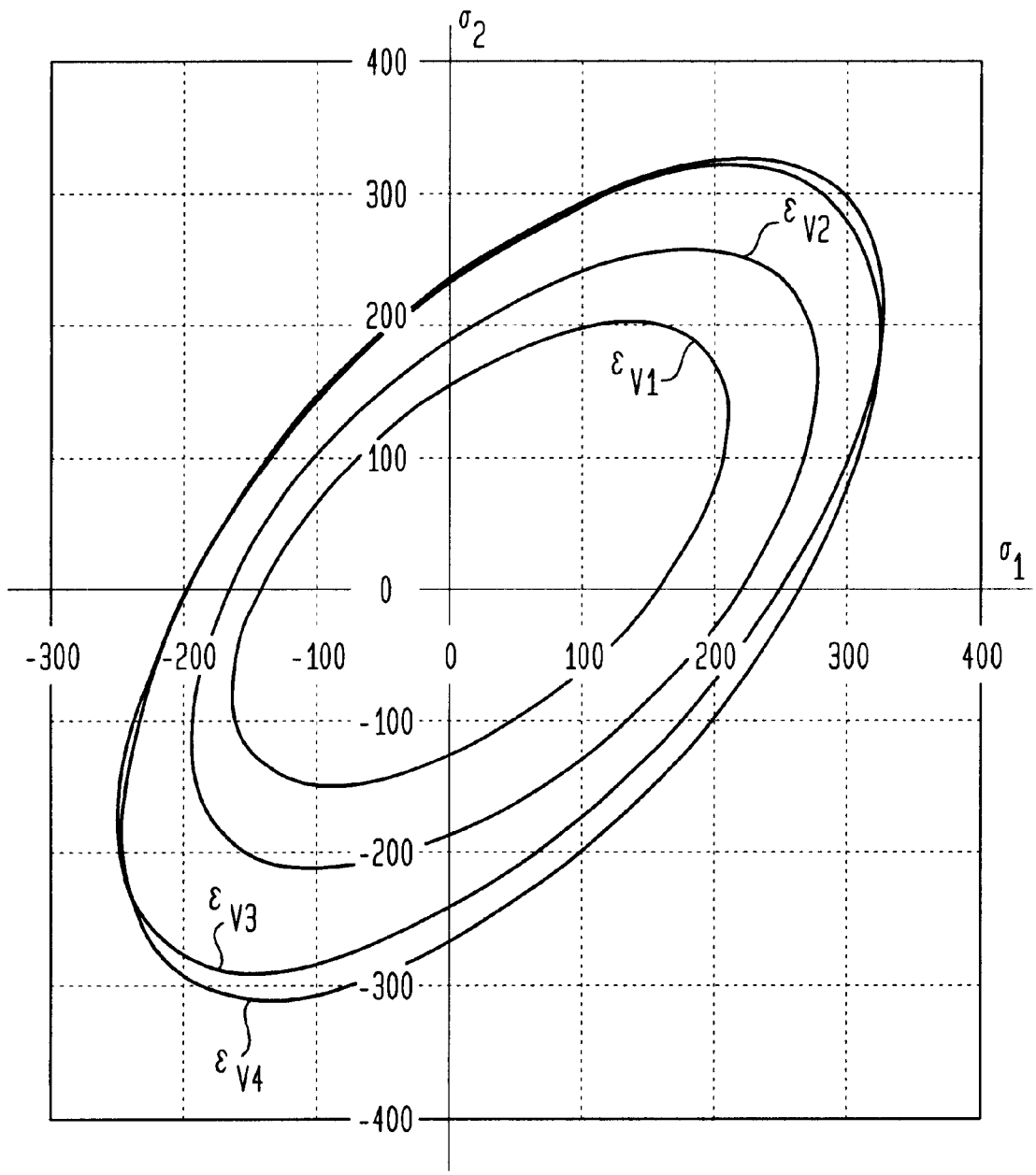

Thus, FIG. 8 shows the flow locus curves of the material which is suitable for deep-drawn parts—i.e., such parts as are predominantly subjected to deep drawing stressing during deformation. The parameters $\epsilon_{V1}$, $\epsilon_{V2}$, $\epsilon_{V3}$, $\epsilon_{V4}$ represent plastic comparative elongation, as described hereinbefore.

It was also found that for bending operations materials having an elliptical flow locus curve are unsuitable whose displacement of center in both axes in the negative direction is >20%. Lastly, it was found that the angle of inclination α of the elliptical flow locus curves has less effect on the three aforementioned shaping suitabilities, but merely boosts the preferential direction of the material.

What is claimed is:

1. A process for determining biaxial shaping behavior of metallic material comprising the steps of:
   (a) producing an area of practically homogeneous deformation in a primary sample by tensile stressing along an axis;
   (b) taking a plurality of secondary samples from the area of practically homogeneous deformation in the primary samples, the plurality of secondary samples having different orientations with respect to the axis of tensile stressing;
   (c) determining tensile and compressive flow limits in the plurality of secondary samples under uniaxial tensile and compressive loading;
   (d) determining in at least one of the secondary samples a plastic longitudinal expansion and a plastic transverse expansion at the tensile or compressive flow limit;
   (e) determining a relationship between the plastic longitudinal and plastic transverse expansion in the at least one secondary sample; and
   (f) determining characteristic parameters of an approximately elliptical flow locus curve from the tensile and compressive flow limits determined in step (c), and from the relationship between the plastic longitudinal and transverse expansion at the tensile or compressive flow limit determined in step (e).

2. The process of claim 1 wherein the area of practically homogeneous deformation in the primary sample is also produced by compressive loading.

3. The process of claim 1 wherein during tensile loading, the primary sample is simultaneously upset transversely to the tensile loading.

4. The process of claim 3 wherein a constant degree of upsetting is maintained in the area of practically homogeneous deformation of the primary sample.

5. The process of claim 3 wherein the tensile loading takes place simultaneously with the upsetting in a wedge-draw test.

6. The process of claim 1 wherein flow locus curves are determined for a plurality of primary samples of identical metallic material, each of which is subjected to different degrees of deformation.

7. The process of claim 1 wherein values with a plastic elongation of 0.02% are used as flow limits.

* * * * *